United States Patent [19]

Konishi et al.

[11] Patent Number: 5,198,452
[45] Date of Patent: Mar. 30, 1993

[54] STYRYL PHRIDYL COMPOUNDS AND THEIR PHARMACEUTICAL COMPOSITIONS

[75] Inventors: Mitsuhiro Konishi, Nakatsu; Minoru Kawakami, Fukuoka; Michio Terasawa; Toshio Hamasaki, both of Nakatsu, all of Japan

[73] Assignee: Yoshitomi Pharmaceutical Industries, Ltd., Osaka, Japan

[21] Appl. No.: 728,128

[22] Filed: Jul. 10, 1991

[51] Int. Cl.$^5$ .................. C07D 213/02; A61K 31/44
[52] U.S. Cl. .................................. 514/357; 546/335
[58] Field of Search ..................... 546/335; 514/357

[56] References Cited

PUBLICATIONS

Chemical Abstracts, vol. 115, Abstract 279,817h, p. 994, Hamazaki et al.

Primary Examiner—C. Warren Ivy
Assistant Examiner—Zinna N. Davis
Attorney, Agent, or Firm—Wenderoth, Lind & Ponack

[57] ABSTRACT

A styryl compound of the formula(I):

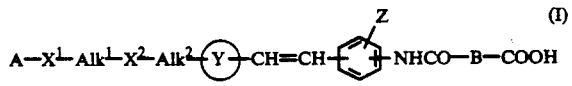

wherein each symbol is as defined in the specification, a pharmaceutically acceptable salt or an ester thereof is disclosed.

Since the compounds of the present invention possess potent and long-lasting leukotriene-antagonistic actions and inhibitory actions against leukotriene, and exhibit better absorption by the oral administration.

Further, the compounds of the present invention possess 5-lipoxygenase-inhibitory actions and/or cyclooxygenase-inhibitory actions, inhibitory actions to biosynthesis of LTB4, chemotactic actions against human leucoccyte, chymase-inhibitory actions, inhibitory actions to release of histamine or antihistamine actions.

Therefore, they are useful as the prophylactic and therapeutic medicines for brochial asthma, chronic bronchitis, atopic dermatitis, allergic rhinitis, allergic arthritis, allergic conjunctivitis, hay fever, urticaria, alimentary allergy, pain, pyretolysis, rheumatoid, thrombosis, coronary vascular diseases, ischemic heart disease, peptic or duodenal ulcer and the like.

5 Claims, No Drawings

STYRYL PHRIDYL COMPOUNDS AND THEIR PHARMACEUTICAL COMPOSITIONS

This is a continuation in-part of PCT/JP90/00905, filed Jul. 12, 1990.

FIELD OF THE INVENTION

The present invention relates to a novel styryl compound, a pharmaceutically acceptable salt thereof or an ester thereof which possesses leukotriene-antagonistic actions and inhibitory actions against leukotriene and further, possesses 5-lipoxygenase-inhibitory actions and/or cyclooxygenase-inhibitory actions, inhibitory actions to biosyntesis of leukotriene B4, chemotactic actions against human leucocytes, chymase-inhibitory actions, inhibitory actions to release of histamine or anti-histamine actions.

BACKGROUND OF THE INVENTION

It is known that chemical madiators such as various leukotrienes, thromboxane A2, various prostaglandins and the like, which are generated in the metabolic route of arachidonic acid, cause certain allergy, inflammation, asthma and the like.

Further, it is considered that ill-balances of these chemical mediators induce various disorders and it is practically expected that antagonists of these chemical mediators in arachidonic acid cascade and/or inhibitors of the biosyntyhesis of such mediators are developed as a medicine.

It is elucidated that leukotrienes which are produced through 5-lipoxygenase, have important functions as chemical mediators and especially, leukotrienes C4, D4 and E4 are components of slow-reacting substance of anaphylaxis (SRS-A), being an important mediator of allergic diseases such as bronchial asthma and inflammations.

Accordingly, the compounds which have leukotriene-antagonistic actions are promising in the treatment of allergic diseases such as bronchial asthma and inflammations.

U.S. Pat. Nos. 4,749,701 and 4,902,700, and European Patent Publication No. 206751-A disclose that certain styryl compounds, certain thiazole compounds and certain phenylalkenylquinoline compounds have leukotriene-antagonistic actions and inhibitory actions against synthesis of leukotriene, respectively.

European Patent No. 173516 discloses N-[4-oxo-2-(1H-tetrazol-5-yl)-4H-1-benzopyran-8-yl]-4-(4-phenyl-butoxy)-benzamide as a leukotriene-antagonist.

European Patent No. 137979 discloses that certain diazinyl ethenyl-phenyl oxamic acid compounds have immunological, anti-inflammatory and anti-allergic activity, and U.S. Pat. No. 4,393,075 discloses that 5-lipoxygenase-inhibitory 6-(12-hydroxy-5,10-dodecadiynyl)-2,3,5-trimethyl-1,4-benzoquinone inhibits to synthesis and releases SRS-A and are useful as an anti-allergic agent.

But, only a few drugs having leukotriene or SRS-A antagonistic activity or inhibitory activity against such biosynthesis, especially by oral administration are known and none is practically used.

Moreover, leukotriene B4 (LTB4) is a chemical mediator on various inflammations (e.g. gout), has strong chemotactic actions against human leucocyte and then a relationship between LTB4 and inflammation has been reported. Further, it is said that myocardial infarction takes a bad turn by the aggregation of a lot of leucocytes. Therefore, it is expected that the 5-lipoxygenase inhibitors and inhibitors to biosynthesis of leukotriene B4 can prevent the aggravation of inflammation or myocardial infarction.

As mentioned above, many kinds of the compounds which specifically act as antagonists of various chemical mediators and inhibitors of the enzymes concerning to the biosynthesis of such chemical mediators have been produced, but no compounds are sufficiently applicable to use as medicines.

On the other hand, it is well-known that histamine is a major causing factor for allergy and inflammation. Recently, the chymase (protease of chymotrypsin type) which exists in granulocyte of mastocyte and involves the release of granular histamine through IgE receptor, has been investigated. Accordingly, studies of a new type of anti-allergic agent which inhibits the release of chemical mediator such as histamine leading to inhibition of chymase, have been intensively conducted.

Therefore, it is also desired to develop a single medicine which can regulate multiple chemical mediators, and prevent or treat the allergy, asthma or inflammation.

SUMMARY OF THE INVENTION

The present invention provides a styryl compound which possesses potent and long-lasting leukotriene-antagonistic actions and inhibitory actions against leukotriene, and also exhibits better absorption by the oral administration.

Further, the present invention provides the styryl compounds which possess 5-lipoxygenase-inhibitory actions and/or cyclooxygenase-inhibitory actions, inhibitory actions to biosynthesis of LTB4, chemotactic actions against human leucocyte, chymase-inhibitory actions, inhibitory actions to release of histamine or anti-histamine actions.

Therefore, they are useful as prophylactic or therapeutic medicines for bronchial asthma, chronic bronchitis, atopic dermatitis, allergic rhinitis, allergic arthritis, allergic conjunctivitis, hay fever, urticaria, alimentary allergy, pain, pyretolysis, rheumatoid, thrombosis, coronary vascular diseases, ischemic heart disease, peptic or duodenal ulcer and the like.

The present invention also provides a pharmaceutical composition comprising an effective amount of the styryl compound of the present invention, pharmaceutical acceptable salts or esters thereof.

DETAILED DESCRIPTION OF THE INVENTION

The present invention relates to a styryl compound of the formula(I):

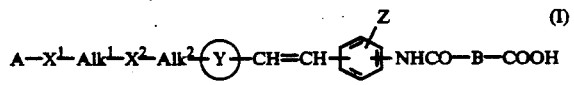

wherein A is hydrogen; an amino group of the formula(a):

(wherein R1 and R2 are the same or different, and respectively represent hydrogen, alkyl or aralkyl, or R1 and R2 together with the adjacent nitrogen atom form hetero-ring); cycloalkyl; aryl; heterocyclic ring; substituted cycloalkyl, aryl hetero-ring or heterocyclic ring by at least one substituent selected from the group consisting of halogen, nitro, amino, monoalkylamino, dialkylamino, hydroxy, alkyl, cycloalkyl, alkenyl, alkenyoxy, alkynyl, aralkyl, alkoxy, halo-alkyl, cyano, alkanoylamino, alkylthio, alkylsulfinyl, alkylsulfonyl, acyl, carbamoyl, monoalkylcarbamoyl, dialkylcarbamoyl, carboxyalkanoylamino, alkoxycarbonylalkanoylamino, phenylsulfonyl, phenylsulfonylamino and a diphenylmethyl group of the formula(b), (c) or (d):

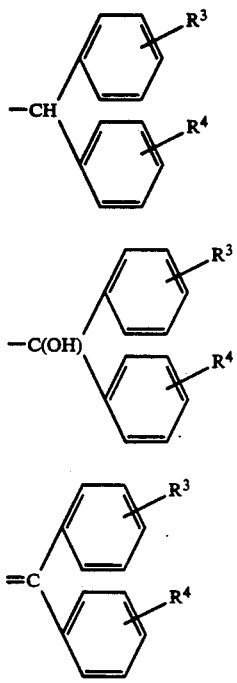

(wherein R3 and R4 are the same or different, and respectively represent hydrogen, halogen, halo-alkyl, amino, nitro, cyano, hydroxy, alkyl or aralkyl); phenylsulfonyl; phenylsulfonylamino; or substituted phenylsulfonyl or phenylsulfonylamino by at least one substituent selected from the group consisting of halogen, nitro, amino, hydroxy, alkyl, alkoxy, halo-alkyl and cyano;

Alk1 and Alk2 are the same or different, respectively represent single bond, alkylene or alkenylene;

X1 and X2 are the same or different, and respectively represent single bond, oxygen, —S(O)n— (wherein n is integer of 0 to 2), —CO—, —N(R5)—, —CON(R6)—, —N(R7)CO—, —CH(OR8)— (wherein R5, R6 and R7 are the same or different, respectively represent hydrogen, alkyl or aralkyl, R8 represents hydrogen, alkyl or acyl);

Y ring represents aryl; heteroaromatic ring; substituted aryl or heteroaromatic ring by at least one substituent selected from the group consisting of halogen, nitro, amino, hydroxy, alkyl, alkoxy, halo-alkyl and cyano;

B represents single bond, straight- or branched-chain alkylene having 1 to 8 carbon atoms, alkenylene having 2 to 8 carbon atoms or cycloalkylene having 3 to 7 carbon atoms;

Z represents hydrogen, halogen, alkyl, alkoxy, halo-alkyl, alkylthio, alkylsulfinyl or alkylsulfonyl; a pharmaceutically acceptable salt or an ester thereof.

In the difinitions of the above symbols, halogens mean chlorine, bromine, fluorine and iodine; alkyls mean straight- or branched-chain alkyls having 1 to 6 carbon atoms such as methyl, ethyl, propyl, isopropyl, butyl, isobutyl, sec-butyl, tert-butyl, pentyl, isopentyl, neopentyl, hexyl and the like; halo-alkyls mean above-mentioned alkyl substituted by 1 to 5 halogens such as trifluoromethyl, 2,2,2-trifluoroethyl, 2,2,3,3,3-pentafluoropropyl and the like; alkoxys mean straight- or branched-chain alkoxys having 1 to 6 carbon atoms such as methoxy, ethoxy, propoxy, isopropoxy, butoxy, isobutoxy, sec-butoxy, tert-butoxy, pentyloxy, isopentyloxy, neopentyloxy, hexyloxy and the like; cycloalkyls mean cycloalkyls having 3 to 7 carbon atoms such as cyclopropyl, cyclobutyl, cyclopentyl, cyclohexyl, cycloheptyl; straight- or branched-chain alkylenes having 1 to 8 carbon atoms mean methylene, ethylene, trimethylene, propylene, tetramethylene, pentamethylene, hexamethylene, heptamethylene, octamethylene, methylmethylene, ethylmethylene, dimethylmethylene, diethylmethylene, dimethylethylene, diethylethylene, dimethyltrimethylene, diethyltrimethylene, dimethyltetramethylene, diethyltetramethylene and the like; alkylenes mean straight- or branched-chain alkylenes having 1 to 20 carbon atoms including the above mentioned straight- or branched-chain alkylenes having 1 to 8 carbon atoms and further nonamethylene, decamethylene, undecamethylene, dodecamethylene, tridecamethylene, tetradecamethylene, pentadecamethylene, hexadecamethylene, heptadecamethylene, octadecamethylene, nonadecamethylene, icosamethylene and the like; alkenylenes having 2 to 8 carbon atoms mean vinylene, propenylene, butenylene, pentenylene, hexenylene, octenylene and the like; alkenylenes mean alkenylenes having 2 to 20 carbon atoms including the above mentioned alkenylenes having 2 to 8 carbon atoms and further nonenylene, decenylene, undecenylene, dodecenylene, tridecenylene, tetradecenylene, pentadecenylene, hexadecenylene, heptadecenylene, octadecenylene, nonadecenylene, icosadecenylene and the like; alkenyls mean alkenyls having 2 to 8 carbon atoms vinyl, propenyl, butenyl, pentenyl, hexcenyl, octenyl and the like; alkenyloxys in which the alkenyl moiety bears 2 to 8 carbon atoms includes vinyloxy, propenyloxy, butenyloxy, pentenyloxy, hexenyloxy, octenyloxy and the like; alkynyls mean alkynyl having 2 to 8 carbon atoms such as propynyl, butynyl, pentynyl, hexynyl, octynyl and the like; aralkyls mean benzyl, 1-phenylethyl, 2-phenylethyl, 3-phenylpropyl, 4-phenylbutyl; substituted benzyl. 1-phenylethyl, 2-phenylethyl, 3-phenylpropyl or 4-phenylbutyl by 1 to 3 substituents selected from the group consisting of halogen, alkyl having 1 to 8 carbon atoms, alkoxy having 1 to 8 carbon atoms, trifluoromethyl, amino, nitro and cyano; acyls mean acetyl, propionyl, butyryl, valeryl, pivaloyl, benzoyl, phenylacetyl, phenylpropionyl, phenylbutyryl and the like; alkylthios mean methylthio, ethylthio, propylthio, isopropylthio, butylthio, isobutylthio, sec-butylthio, tert-butylthio, pentylthio, isopentylthio, neopentylthio, hexylthio and the like; alkanoylaminos in which the alkanoyl moiety is straight- or branched-chain alkanoyl having 2 to 8 carbon atoms mean acetylamino, propionylamino, butyrylamino, valerylamino, pivaloylamino, 3-ethylvalerylamino and the like; carboxyalkanoylaminos in which the alkanoyl moiety is straight- or branched chain alkanoyl having 2 to 8 carbon atoms mean carboxyacetylamino, carboxypropionylamino, carboxybutyrylamino, carboxyvalerylamino, 3-carboxy-2,2-dimethylpropionylamino, 3-carboxy-3-ethylvalerylamino and the like; aryls mean phenyl, 1-naphthyl, 2-naphthyl and the like; monoalkylcarbamoyls mean methylcarbamoyl, ethylcarbamoyl, propylcarbamoyl, isopropylcarbamoyl, butylcarbamoyl, isobutylcarbamoyl, tert-butylcarbamoyl, pentylcarbamoyl, hexylcarbamoyl and the like; dialkylcarbamoyls mean dimethylcarbamoyl, diethylcarbamoyl, dipropylcarbamoyl, diisopropylcarbamoyl, dibutylcarbamoyl, diisobutylcarbamoyl, di-tert-butylcarbamoyl, dipentylcarbamoyl, dihexylcarbamoyl, N-methyl-N-ethylcarbamoyl, N-methyl-N-propylcarbamoyl, N-methyl-N-butylcarbamoyl, N-methyl-N-tert-butylcarbamoyl, N-methyl-N-pentylcarbamoyl, N-methyl-N-hexylcarbamoyl and the like; heterocyclic rings mean pyrrolidinyl, piperidyl, thienyl, furyl, pyrrolyl, pirazolyl, imidazolyl, oxazolyl, isooxazolyl, pyridyl, pyridazinyl, pyrimidynyl, pyrazinyl, benzodioxanyl, benzoxazinyl, benzothiazinyl, quinolyl and the like; heteroaromatic rings mean thienyl, furyl, pyrrolyl, pyrazolyl, imidazolyl, oxazolyl, isooxazolyl, pyridyl, pyridazinyl, pyrimidynyl, pyrazinyl, benzodioxanyl, benzoxazinyl, benzothiazinyl, quinolyl and the like; the hetero-rings formed by R1 and R2 together with the adjacent nitrogen atom may additionally contain, as a ring member, the heteroatoms such as nitrogen, oxygen, sulfur and the like, and can be optionally substituted by substituents selected from the group consisting of halogen, nitro, amino, hydroxy, alkyl, cycloalkyl, alkenyl, alkenyloxy, alkynyl, aralkyl, alkoxy, halo-alkyl, cyano, alkanoylamino, alkylthio, acyl, carbamoyl, carboxyalkanoylamino, phenylsulfonyl, phenylsulfonylamino and the diphenylmethyl group of formula(b), (c) or (d):

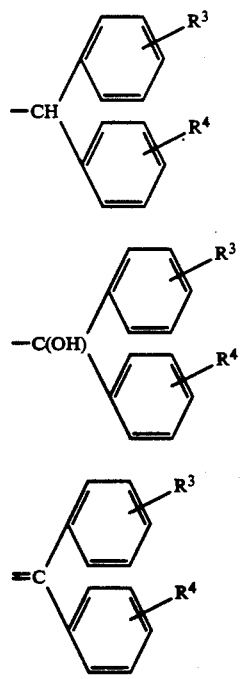

(wherein R3 and R4 are the same or different, and respectively represent hydrogen, halogen, halo-alkyl, amino, nitro, cyano, hydroxy, alkyl or aralkyl), and include, for example, 1-pyrrolidinyl, piperidino, morpholino, thiomorpholino, 1-piperazinyl, 1-homopiperazinyl and the like.

The salts of the styryl compound of the present invention include pharmaceutically acceptable salts such as acid addition salts with inorganic or organic acid (hydrochloric acid, hydrobromic acid, sulfuric acid, phosphoric acid, nitric acid, acetic acid, propionic acid, lactic acid, oxalic acid, fumaric acid, maleic acid, mandelic acid, citric acid, tartaric acid, succinic acid, glycolic acid, malic acid, ascorbic acid, methanesulfonic acid, p-toluenesulfonic acid etc.), salts with an alkali metal (sodium, potassium etc.), salts with an alkaline earth metal (calcium, magnesium etc.), salts with quaternary ammonium, salts with amino acid (lysine etc.) and salts with amine (triethylamine, diethanolamine etc.).

The ester of the styryl compound of the present invention includes alkyl ester, aralkyl ester and, further, the ester which is readily hydrolyzable in vivo and may be easily decomposed to free carboxylic acid in vivo, for example, an alkanoyloxyalkyl ester such as acetoxymethyl ester, pivaloyloxymethyl ester, 1-acetoxyethyl ester or 1-pivaloyloxyethyl ester; an alkoxycarbonyloxyalkyl ester such as ethoxycarbonyloxymehtyl ester or 1- ethoxycarbonyloxyethyl ester; a phtalidyl ester such as phthalidyl ester or dimethoxyphthalidyl ester; a carbamoylalkyl ester such as carbamoylmethyl ester, carbamoylethyl ester, N-methylcarbamoylmethyl ester, N,N-dimethylcarbamoylmethyl ester or N,N-diethylcarbamoylmethyl ester; an alkoxyalkyl ester such as methoxymethyl ester or methoxyethyl ester; 5-methyl-2-oxo-1,3-dioxolen-4-ylmethyl ester; an aminoalkyl ester such as aminomethyl ester, aminoethyl ester or aminopropyl ester; an alkylaminoalkyl ester such as methylaminomethyl ester, methylaminoethyl ester, methylaminopropyl ester, ethylaminomethyl ester, ethylaminoethyl ester, ethylaminopropyl ester, dimethylaminomethyl ester, dimethylaminoethyl ester, dimethylaminopropyl ester, diethylaminomethyl ester, diethylaminoethyl ester or diethylaminopropyl ester; an morpholinoalkyl ester such as morpholinoethyl ester; an piperidinoalkyl ester such as piperidinoethyl ester; or an alkylphenylamino ester such as methylphenylamino ester.

Furthermore, the present invention also embraces the corresponding hydrate form or other solvate forms of the compounds of formula(I).

The compounds of the formula(I) include geometrical isomers, i.e. (E)-form isomer, (Z)-form isomer and a mixture thereof. In the present invention, a more desirable geometrical isomer is (E)-form isomer.

When the compounds of the formula(I) have one or more asymmetric carbon atoms, racemates, diastereomers and individual optical isomers thereof are encompassed in the present invention.

The present invention are also provides the styryl compounds of formula(I'):

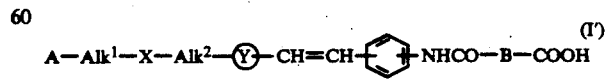

wherein A is hydrogen; an amino group of the formula(a):

(wherein R1 and R2 are the same or different, and respectively represent hydrogen, alkyl or aralkyl, or R1 and R2 together with the adjacent nitrogen atom form hetero-ring); cycloalkyl; aryl; heterocyclic ring; substituted cycloalkyl, aryl, hetero-ring or heterocyclic ring by at least one substituent selected from the group consisting of halogen, nitro, amino, hydroxy, alkyl, cycloalkyl, alkenyl, alkenyloxy, alkynyl, aralkyl, alkoxy, haloalkyl, cyano, alkanoylamino, alkylthio, acyl, carbamoyl, carboxyalkanoylamino, phenylsulfonyl, phenylsulfonylamino and a diphenylmethyl group of the formula(b):

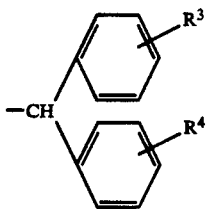
(b)

(wherein R3 and R4 are the same or different, and respectively represent hydrogen, halogen, halo-alkyl, amino, nitro, cyano, hydroxy, alkyl or aralkyl); phenylsulfonyl; phenylsulfonylamino; or substituted phenylsulfonyl or phenylsulfonylamino by at least one substituent selected from the group consisting of halogen, nitro, amino, hydroxy, alkyl, alkoxy, halo-alkyl and cyano;

Alk1 and Alk2 are the same or different, respectively represent single bond, alkylene or alkenylene;

X represents single bond, oxygen, —S(O)n— (wherein n is integer of 0 to 2), —CO—, —N(R5)—, —CON(R6)—, —N(R7)CO— (wherein R5, R6 and R7 are the same or different, respectively represent hydrogen or alkyl);

Y ring represents aryl; heteroaromatic ring; substituted aryl or heteroaromatic ring by at least one substituent selected from the group consisting of halogen, nitro, amino, hydroxy, alkyl, alkoxy, haloalkyl and cyano;

B represents single bond, straight- or branched-chain alkylene having 1 to 8 carbon atoms, alkenylene having 2 to 8 carbon atoms or cycloalkylene having 3 to 7 carbon atoms; a pharmaceutically acceptable salt or an ester thereof.

As the preferable compounds, the present invention provides the compounds of formula (I) wherein Y ring represents pyridyl, pharmaceutically acceptable salts or esters thereof.

One group of more preferable compounds are (a) 2-[(E)-2-(3-(3-carboxy-4-ethylvalerylamino)phenyl) ethenyl]-6-[4-(4-isopropylphenyl)butoxy]methylpyridine (b) 2-[(E)-2-(3-(3-carboxy-3-ethylvalerylamino)phenyl) ethenyl]-6-(4-phenylbutoxy)methylpyridine (c) 2-[(E)-2-(3-(3-carboxy-3-ethylvalerylamino)phenyl) ethenyl]-6-[4-(4-butylphenyl)butoxy]methylpyridine (d) 2-[(E)-2-(3-(3-carboxy-3-ethylvalerylamino)phenyl) ethenyl]-6-[4-(4-fluorophenyl)butoxy]methylpyridine (e) 2-[(E)-2-(3-(3-carboxy-3-ethylvalerylamino)phenyl) ethenyl]-6-[4-(4-isobutylphenyl)butoxy]methylpyridine (f) 2-[(E)-2-(3-(3-carboxy-3-ethylvalerylamino)phenyl) ethenyl]-6-[4-(4-ethylphenyl)butoxy]methylpyridine (g) 2-[(E)-2-(3-(3-carboxy-3-ethylvalerylamino)phenyl) ethenyl]-6-[4-(4-ethoxyphenyl)butoxy]methylpyridine (h) 2-[(E)-2-(3-(3-carboxy-3-ethylvalerylamino)phenyl) ethenyl]-6-[4-(4-butoxyphenyl)butoxy]methylpyridine (i) 2-[(E)-2-(3-(3-carboxy-3-ethylvalerylamino)phenyl) ethenyl]-6-[4-(4-propoxyphenyl)butoxy]methylpyridine (j) 2-[(E)-2-(3-(3-carboxy-3-ethylvalerylamino)phenyl) ethenyl]-6-[4-(4-propylphenyl)butoxy]methylpyridine (k) 2-[(E)-2-(3-(3-carboxy-3-ethylvalerylamino)phenyl) ethenyl]-6-[4-(4-isopentyloxyphenyl)butoxy]methylpyridine (l) 2-[(E)-2-(3-(3-carboxy-3-ethylvalerylamino)phenyl) ethenyl]-6-(6-phenylhexyl)pyridine (m) 2-[(E)-2-(3-(3-carboxy-3-ethylvalerylamino)phenyl) ethenyl]-6-[6-(4-ethylphenyl)hexyl]pyridine (n) 2-[(E)-2-(3-(3-carboxy-3-ethylvalerylamino)phenyl) ethenyl]-6-[6-(4-n-butylphenyl)hexyl]pyridine (o) 2-[(E)-2-(3-(3-carboxy-3-ethylvalerylamino)phenyl) ethenyl]-6-[6-(4-n-butoxyphenyl)hexyl]pyridine (p) 2-[(E)-2-(3-(3-carboxy-3-ethylvalerylamino)phenyl) ethenyl]-6-[6-(4-isopentyloxyphenyl)hexyl]pyridine (q) 2-[(E)-2-(3-(3-carboxy-3-ethylvalerylamino)phenyl) ethenyl]-6-(5-phenylpentyloxy)pyridine (r) 2-[(E)-2-(3-(3-carboxy-3-ethylvalerylamino)phenyl) ethenyl]-6-[5-(4-ethylphenyl)pentyloxy]pyridine (s) 2-[(E)-2-(3-(3-carboxy-3-ethylvalerylamino)phenyl) ethenyl]-6-[5-(4-n-butylphenyl)pentyloxy]pyridine (t) 2-[(E)-2-(3-(3-carboxy-3-ethylvalerylamino)phenyl) ethenyl]-6-[5-(4-n-butoxyphenyl)pentyloxy]pyridine, and (u) 2-[(E)-2-(3-(3-carboxy-3-ethylvalerylamino)phenyl) ethenyl]-6-[5-(4-isopentyloxyphenyl)pentyloxy]pyridine.

Another group of more preferable compounds are (1) 2-[(E)-2-(3-(3-carboxy-3-ethylvalerylamino)phenyl) ethenyl]-6-[4-(4-(3-pyridylmethyloxy)phenyl)butoxy]methylpyridine (2) 2-[(E)-2-(3-(3-carboxy-3-ethylvalerylamino)phenyl) ethenyl]-6-[4-(4-(3-(1-imidazolyl)propoxy)phenyl)butoxy]methylpyridine (3) 2-[(E)-2-(3-(3-carboxy-3-ethylvalerylamino)phenyl) ethenyl]-6-[4-(3,4-dihydroxyphenyl)butoxy]methylpyridine (4) 2-[(E)-2-(3-(3-carboxy-3-ethylvalerylamino)phenyl) ethenyl]-6-[4-(4-hydroxy-3-methylphenyl)butoxy]methylpyridine (5) 2-[(E)-2-(3-(3-carboxy-3-ethylvalerylamino)phenyl) ethenyl]-6-[4-(4-hydroxy-3,5-dimethylphenyl)butoxy]methylpyridine (6) 2-[(E)-2-(3-(3-carboxy-3-ethylvalerylamino)phenyl) ethenyl]-6-[4-(4-hydroxy-3,5-di-tert-butylphenyl)butoxy]methylpyridine (7) 2-[(E)-2-(3-(3-carboxy-3-ethylvalerylamino)phenyl) ethenyl]-6-[6-(4-hydroxy-3,5-di-tert-butylphenyl)hexyl]pyridine (8) 2-[(E)-2-(3-(3-carboxy-3-ethylvalerylamino)phenyl) ethenyl]-6-[6-(3,4-dihydroxyphenyl)hexyl]pyridine (9) 2-[(E)-2-(3-(3-carboxy-3-ethylvalerylamino)phenyl) ethenyl]-6-[6-(4-hydroxy-3-methylphenyl)hexyl]pyridine

(10) 2-[(E)-2-(3-(3-carboxy-3-ethylvalerylamino)phenyl) ethenyl]-6-[6-(4-hydroxy-3,5-dimethylphenyl)hexyl]pyridine

(11) 2-[(E)-2-(3-(3-carboxy-3-ethylvalerylamino)phenyl) ethenyl]-6-[5-(4-hydroxy-3,5-dimethylphenyl)pentyloxy]pyridine

(12) 2-[(E)-2-(3-(3-carboxy-3-ethylvalerylamino)phenyl) ethenyl]-6-[4-(4-hydroxy-3,5-dimethylphenyl)butoxy]pyridine

(13) 2-[(E)-2-(3-(3-carboxy-3-ethylvalerylamino)phenyl) ethenyl]-6-[4-(4-hydroxy-3-methylphenyl)pentyloxy]pyridine, and

(14) 2-[(E)-2-(3-(3-carboxy-3-ethylvalerylamino)phenyl) ethenyl]-6-[3-(4-hydroxy-3,5-di-tert-butylphenoxy) propoxy]methylpyridine.

The compounds of formula(I) of the present invention can be prepared by reacting the compound of formula(II):

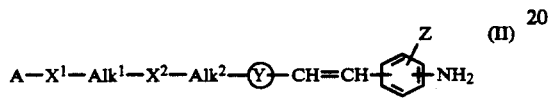

wherein each symbol is as defined above, with a cyclic acid anhydride compound of the formula(III):

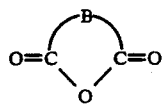

wherein B is as defined above, or an acid halide compound of the formula(IV):

wherein Hal is chloride, bromine or iodine, R8 is alkyl or aralkyl and B is as defined above, if necessary, subjecting the obtained ester compound to hydrolysis or inducing the obtained carboxylic acid compound to the ester.

The reaction with the cyclic acid anhydride of formula(III) can be carried out under ice-cooling to the boiling point of solvent used, preferably at room temperature to 60° C. in a solvent such as an ether (e.g. 1,2-dimethoxyethane, tetrahydrofuran or dioxane) and a halogenated hydrocarbon (e.g. chloroform or dichloromethane).

The reaction with the acid halide Of formula (IV) can be carried out at −10° C. to the boiling point of solvent used in a suitable solvent in the presence of a base such as an organic base (e.g. trimethylamine or pyridine) and an inorganic base (e.g. potassium carbonate, sodium carbonate, sodium hydrogencarbonate or potassium hydrogencarbonate) or without a base.

The hydrolysis reaction of ester can be carried out in a solvent miscible with water in the presence of an acid (e.g. hydrochloric acid, sulfuric acid, hydrobromic acid or phosphoric acid) or an alkali (e.g. sodium hydroxide, potassium hydroxide or potassium hydrogencarbonate) in a conventional manner.

Further, the esterification of the carboxylic acid compound of the formula(I) can be carried out reacting the carboxylic acid compound of formula(I) with the compound of formula(V):

$$R-X^3 \qquad (V)$$

wherein R is alkyl, aralkyl or the ester residue which is readily hydrolyzable in vivo, X3 is halogen (e.g. chlorine, bromine or iodine) or an organic sulfonyloxy group (e.g. methylsulfonyloxy, benzenesulfonyloxy or p-toluenesulfonyloxy), in a conventional manner.

Moreover, the compound of formula(I) wherein X is sulfinyl (—SO—) or sulfonyl (—SO2—) can be prepared by subjecting the compound of formula(I) wherein X is —S— to oxidative reaction in a suitable solvent in the presence of an oxidizing agent (e.g. peracetic acid, perbenzoic acid, m-chloroperbenzoic acid, sodium hypobromite or hydrogen peroxide).

The intermediate compounds of formula(II) of the present invention can be prepared by subjecting the compound of formula(VI):

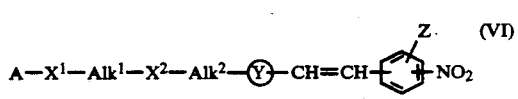

wherein each symbol is as defined above, to reductive reaction.

The reductive reaction can be carried out by reacting with zinc, iron, tin or tin(II) chloride in an acidic condition, subjecting to catalytic reduction or reacting with sodium hydrosulfite or sodium dithionite.

The intermediate compounds of formula(VI) of the present invention can be prepared by reacting the compound of formula(VII):

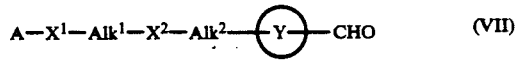

wherein each symbol is as defined above, with the compound of formula(VIII):

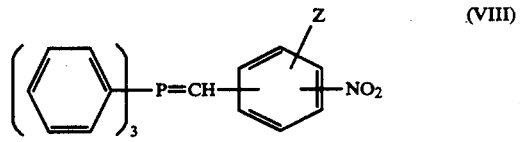

wherein Z is as defined above, according to Wittig reaction.

The compounds of formula(vIII) can be prepared by treating a phosphonium compound obtained by reacting, for example, triphenylphosphine and nitrophenyl halide(substituted by Z) with a base such as alkali hydroxide, alkali metal hydroxide, alkali metal alkoxide, alkali metal amide, organic lithium or alkali metal carbonate.

The compounds of formula(vIII) can be also prepared through a phosphonate compound obtained from triphenylphosphite.

The Wittig reaction is usually carried out in a solvent such as a non-protonic polar solvent (e.g. dimethylformamide or dimethyl sulfoxide), an alcohol (e.g. methanol, ethanol, isopropyl alcohol), an ether (e.g. tetrahydrofuran), a hydrocarbon (e.g. benzene, toluene), a halogenated hydrocarbon (e.g. chloroform, dichloromethane), water or their mixed solvents at −10° C. to the boiling point of the solvent used for 1 to 10 hours.

The intermediate compounds of formula(VI) can be prepared by reacting the compound of formula(IX):

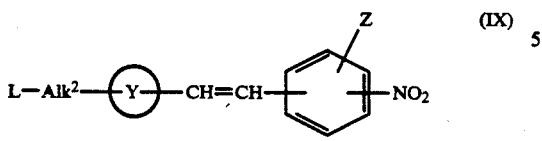

wherein L is a reactive residue such as chlorine, bromine, iodine, methanesulfonyloxy, p-toluenesulfonyloxy and other symbols are as defined above, with the compound of formula:

wherein each symbol is as defined above.

The reaction can be carried out in a suitable solvent (e.g. dimethylformamide, dimethyl sulfoxide, acetone, methyl ethyl ketone, benzene, toluene or xylene). Further, the reaction can be preferably carried out in the presence of a suitable base (e.g. alkali metal hydroxide, alkali metal alkoxide, alkali metal carbonate or alkali metal amide) at room temperature to the boiling point of the solvent used.

Especially, the intermediate compounds of formula(VI) wherein both of X1 and X2 are single bonds and Alk2 is ethylene can be prepared by the following steps (1) through (3).

Step(1): The compound of the formula(XIII):

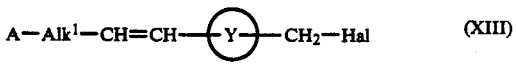

wherein Hal is halogen and other symbols are as defined above, can be prepared by reacting a compound of the formula(XI):

wherein each symbol is as defined above, with a compound of the formula(XII):

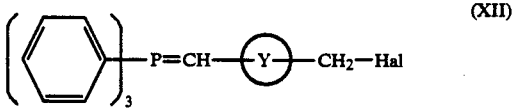

wherein each symbol is as defined above, according to Wittig reaction.

The Wittig reaction can be carried out in similar manner as above-mentioned. Preferably, the reaction can be carried out at room temperature for 4 to 6 hours in the presence of sodium hydroxide as a base in tetrahydrofuran as a solvent.

Step(2) A compound of formula(XVI):

wherein each symbol is as defined above, can be prepared by subjecting the compound of formula(XIII) to acetoxylation, subjecting an obtained compound of the formula(XIV):

wherein R' represents alkyl, aryl or aralky and other symbols are as defined above, to catalytic reduction and subjecting an obtained compound of the formula(XV):

wherein each symbol is as defined above, to hydrolysis.

In the acetoxylation reaction, a non-protonic polar solvent(e.g. dimethylformamide or dimethyl sulfoxide), an alcohol(e.g. methanol, ethanol, isopropyl alcohol), an ether(e.g. tetrahydrofuran), a hydrocarbon(e.g. benzene, toluene), a halogenated hydrocarbon(e.g. chloroform, dichloromethane), water or their mixed solvents can be used as the solvent and sodium acetate, potassium acetate or acetic anhydride can be used as the acetoxylation reagent. Preferably, the acetoxylation reaction can be carried out by reacting with sodium acetate at 80° C. for 10 to 24 hours in the mixed solvent with ethanol and dimethyl sulfoxide.

In the catalytic reduction, an alcohol(e.g. methanol, ethanol, isopropyl alcohol), an ether(e.g. tetrahydrofuran), a hydrocarbon(e.g. benzene, toluene), water, acetic acid and their mixed solvents can be used as the solvent and platinum, palladium, nickel and the like can be used as the catalyst. Preferably, the catalytic reduction can be carried out at room temperature for 2 to 11 hours in the mixed solvent with alcohol, water and acetic acid in the presence of palladium-carbon as a catalyst.

In the hydrolysis reaction, an alcohol(e.g. methanol, ethanol, isopropyl alcohol), an ether(e.g. tetrahydrofuran), a hydrocarbon(e.g. benzene, toluene), a non-protonic polar solvent(e.g. dimethylformamide, dimethyl sulfoxide), water or their mixed solvents can be used as the solvent and an alkali metal hydroxide, an alkali metal alkoxide, an alkali metal amide, an alkali metal carbonate can be used as the base. Preferably, the hydrolysis reaction can be carried out under reflux for 1 to 4 hours in the presence of potassium hydride in the mixed solvent of methanol and water.

Step(3): The compound of formula(VI) can be prepared by subjecting the compound of formula(XVI) to halogenation, reacting an obtained compound of the formula(XVII):

wherein each symbol is as defined above, with triphenylphosphine and then reacting an obtained compound of the formula(XVIII):

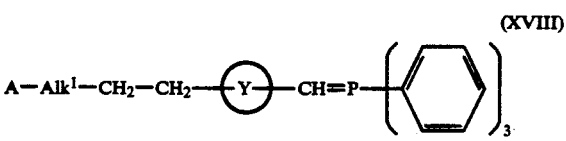

wherein each symbol is as defined above, with nitrobenzaldehyde, according to Wittig reaction.

In the halogenation reaction, a halogenated hydrocarbon(e.g. chloroform, dichloromethane), a hydrocarbon(e.g. benzene, toluene), an ether(e.g. tetrahydrofuran) can be used as the solvent and thionyl chloride, phosphorous tribromide, hydrogen chloride solution, hydrogen bromide solution can be used as the halogenation reagent. Preferably, the halogenation reaction can be carried out under heating for 1 to 2 hours in the presence of thionyl chloride in chloroform.

The reaction with triphenylphosphine can be carried out in a solvent such as a hydrocarbon(e.g. benzene, toluene), an ether(e.g. tetrahydrofuran), a non-protonic polar solvent(e.g. dimethylformamide, dimethyl sulfoxide) at room temperature to boiling point of the solvent used, preferably, under reflux for 5 to 20 hours in toluene.

In Wittig reaction, the base for converting a phosphonium salt compound into a ylide compound includes an alkali hydroxide, an alkali metal hydroxide, an alkali metal alkoxide, an alkali metal amide, an organic lithium, an alkali metal carbonate and a non-protonic polar solvent(e.g. dimethylformamide, dimethyl sulfoxide), an alcohol(e.g. methanol, ethanol, isopropyl alcohol), an ether(e.g. tetrahydrofuran), a hydrocarbon(e.g. benzene, toluene), a halogenated hydrocarbon(e.g. chloroform, dichloromethane), water or their mixed solvents can be used as the solvent.

Further, the ylide compound drived from triphenylphosphine compound and the phosphate-ylide compound derived from triphenylphosphine in a modified method of Wittig reaction, can be used as ylide. Preferably, the modified Wittig reaction can be carried out at $-10°$ to $-5°$ C. in a mixed solvent of dimethylformamde and tetrahydrofuran in the presence of sodium hydride as a base, by standing an obtained ylide compound at room temperature for 0.5 to 2 hours, adding dropwise a nitrobenzaldehyde compound of the formula(e):

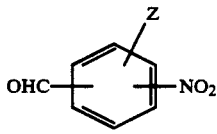
(e)

wherein Z is as defined above, at room temperature thereto and stirring at room temperature for 5 to 10 hours.

Moreover, the intermediate compounds of formula(VI) wherein X1 represents single bond, X2 represents oxygen, Alk2 represents single bond and Y ring represents pyridyl can be prepared by the following step(4) through (6).

Step(4): The compound of the formula(XXII):

(XXII)

wherein Y' ring represents N-oxidized pyridyl and other symbols are as defined above, can be prepared by reacting a compound of the formula(XIX):

(XIX)

wherein each symbol is as defined above, with a compound of the formula(XX):

(XX)

wherein Y ring is as defined above, in sodium hydride/dimethyl sulfoxide and subjecting an obtained compound of the formula(XXI):

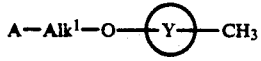
(XXI)

wherein each symbol is as defined above, to oxidation.

The reaction of the compounds of formula(XIX) with the compounds of formula(XX) can be carried out under nitrogen atmosphere in a suitable solvent (e.g. dimethylformamide or dimethyl sulfoxide) in the presence of a base (e.g. sodium hydroxide, potassium hydroxide, sodium carbonate, potassium carbonate, sodium hydrogencarbonate or potassium hydrogencarbonate) at room temperature to the boiling point of the solvent used for 0.5 to 10 hours. Preferably, a solution of sodium hydride in dimethyl sulfoxide kept at 70° C. is stirred at the same temperature for 0.5 to 1 hour. After cooling to room temperature, to the mixture is added the compound of formula(XX) and stirred at same temperature for 0.5 to 1 hour. Further, one equivalent of tetrahydrofuran to dimethyl sulfoxide is added to the reaction mixture and chilled. Further, to the reaction mixture is added the compound of formula(XIX), stirred at the same temperature for 1 to 2 hours and further stirred at room temperature for 4 to 5 hours. After completion of the reaction, the objective compound of formula(XXI) can be purified by chromatography on silica gel by passing chloroform.

The oxidation reaction can be carried out at 10° to 100° C. for 1 to 50 hours in the presence of an oxidizing agent (e.g. peracetic acid, perbenzoic acid, m-chloroperbenzoic acid, sodium hypochloride, sodium hypobromite) in a suitable solvent (e.g. acetic acid). Preferably, the compound of formula(XXII) can be obtained by reacting the compound of formula(XXI) with 30% of hydrogen peroxide at 85° to 90° C. for 6 to 48 hours and by reacting the compound of the formula(XXI) with one equivalent of m-chloroperbenzoic acid at room temperature for 1 to 24 hours.

Step(5): A compound of the formula(XXIII):

(XXIII)

wherein each symbol is as defined above, can be prepared by reacting the compound of formula(XXII) with an acetoxylation reagent such as sodium acetate, potassium acetate or acetic anhydride in a suitable solvent such as a non-protonic polar solvent (e.g. dimethylformamide or dimethyl sulfoxide), an alcohol (e.g. methanol, ethanol or isopropyl alcohol), an ether (e.g. tetrahydrofuran), a hydrocarbon (e.g. benzene or toluene), a halogenated hydrocarbon (e.g. chloroform or dichloromethane), water or their mixed solvents. Preferably, the compound of formula(XXIII) can be obtained by reacting the compound of formula(XXII) under reflux for 1 to 3 hours in acetic anhydride.

Step(6): The obtained compound of formula(XXIII) can be converted into the compound of formula(VI) by subjecting the compounds of formula(XXIII) to hydrolysis, subjecting to halogenation and then subjecting to Wittig reaction.

The hydrolysis reaction, halogenation reaction and Wittig reaction can be carried out the same manner as mentioned above.

The compounds of the present invention have geometrical isomers, and these individual (E)-form and (Z)-form isomers can be separated by the conventional method such as fractional crystallization or chromatography.

When thus obtained compounds of formula(I) have chiral carbon atoms, they are usefully obtained as racemates or diastereomers. These racemates or diastereomers can be resolved into the optical isomers by the conventional method such as fractional crystallization or chromatography. These optical isomers can be also produced by employing the optically active starting compounds.

The compounds of the formula(I) can be converted into their pharmaceutically acceptable salts by treating them with an inorganic acid (hydrochloric acid, hydrobromic acid, sulfuric acid, phosphoric acid, nitric acid, etc.), an organic acid (acetic acid, propionic acid, lactic acid, oxalic acid, fumaric acid, maleic acid, mandelic acid, citric acid, tartaric acid, succinic acid, glycolic acid, malic acid, ascorbic acid, methanesulfonic acid, p-toluenesulfonic acid, etc.), an alkali metal hydroxide (sodium hydroxide, potassium hydroxide, etc.), an alkaline earth metal hydroxide (calcium hydroxide, magnesium hydroxide, etc.), a quaternary ammonium-forming reagent (quaternary ammonium hydroxide, etc.), an amino acid (lysine, etc.) and an amine (triethylamine, diethanolamine, etc.).

The corresponding ester compounds of the formula(I) can be prepared by reacting the carboxylic acid compounds of formula(I) with the halogenated corresponding ester residue.

The carboxylic acid compounds of formula(I) can be also converted into the corresponding ester compounds of formula(I) in a conventional manner.

The present invention is explained below by illustrating experimental examples and working examples, which are not to be construed as limitative, needless to say.

The inhibitory actions to leukotriene of the compounds of the present invention are detailedly described by the following pharmaceutical experimental example.

The test compounds of the present invention are as follows:

Compound A: 2-[(E)-2-(3-(3-carboxy-3-ethylvalerylamino)phenyl)ethenyl]-6-(4-phenylbutoxy)methylpyridine ¼ hydrate Compound B: 2-[(E)-2-(3-(3-carboxy-3-ethylvalerylamino)phenyl)ethenyl]-6-[4-(4-butylphenyl)butoxy]methylpyridine Compound C: 2-[(E)-2-(3-(3-carboxy-3-ethylvalerylamino)phenyl)ethenyl]-6-[4-(4-fluorophenyl)butoxy]methylpyridine ¼ hydrate Compound D: 2-[(E)-2-(3-(3-carboxy-3-ethylvalerylamino)phenyl)ethenyl]-6-[4-(4-ethylphenyl)butoxy]methylpyridine Compound E: 2-[(E)-2-(3-(3-carboxy-3-ethylvalerylamino)phenyl)ethenyl]-6-[4-(4-propylphenyl)butoxy]methylpyridine ¼ hydrate Compound F: 2-[(E)-2-(3-(3-carboxy-3-ethylvalerylamino)phenyl)ethenyl]-6-[4-(4-isopropylphenyl)butoxy]methylpyridine Compound G: 2-[(E)-2-(3-(3-carboxy-3-ethylvalerylamino)phenyl)ethenyl]-6-[4-(4-isobutylphenyl)butoxy]methylpyridine Compound H: 2-[(E)-2-(3-(3-carboxy-3-ethylvalerylamino)phenyl)ethenyl]-6-[4-(4-ethoxyphenyl)butoxy]methylpyridine Compound I: 2-[(E)-2-(3-(3-carboxy-3-ethylvalerylamino)phenyl)ethenyl]-6-[4-(4-propoxyphenyl)butoxy]methylpyridine Compound J: 2-[(E)-2-(3-(3-carboxy-3-ethylvalerylamino)phenyl)ethenyl]-6-[4-(4-butoxyphenyl)butoxy]methylpyridine 3/2 hydrate Compound K: 2-[(E)-2-(3-(3-carboxy-3-ethylvalerylamino)phenyl)ethenyl]-6-[4-(4-isopentyloxyphenyl)butoxy]methylpyridine ¼ hydrate The compound for comparison is as follows:

Compound L: 1-[2-hydroxy-3-propyl-4-(4-(1H-tetrazol-5-yl) butoxy)phenyl]ethanone (LY-171883: U.S. Pat. No. 4,661,505)

EXPERIMENT EXAMPLE 1

The inhibition of contractions of guinea pig terminal ileum induced with leukotriene D4.

Segments of male Hartly guinea pig terminal ileus were mounted under 750 mg tension in a 10 ml organ bath containing a Tyrode solution. To eliminate instrinsic prostaglandin and cholinergic responses, indomethacin (3 $\mu$M) and atropin (0.3 $\mu$M) were incorporated into bathing solution under continuous aeration at 37° C. Isometric measurements were made with an isotonic transducer and recorded on a multipen-recorder. After an equilibration period of 30–60 minutes, isotonic responses were 1 nm LTD4 were recorded until reproducible responses obtained. The submaximal contraction induced by 1 nM LTD4 served as control. Test compounds were dissolved in ethanol (0.1% final concentration) and incubated at various concentrations for 2 minutes before contractions were induced with 1 nM LTD4. The inhibition of contraction was calculated relative to the preceding control contraction. The inhibitory concentration (IC50, g/ml) were calculated graphically. The results are shown in Table 1.

EXPERIMENT EXAMPLE 2

Actions of bronchoconstriction in guinea pigs induced with leukotriene D4.

Resistance to lung inflation was measured by the overflow method of Konzett and Rossler (Naunyn Schmiedebergs Arch. Exp. pathol. Pharmakol., 195, 71–74, 1940), modified by the use of an air pressure transducer. Female Hartley guinea pigs (350–450 g) were anesthetized with urethane (1.5 g/kg, i.p.). An endotracheal tube was inserted in the trachea and connected to an air pump (Matsushita Denko Co., Ltd.) with an exhaust relay of 50 strokes/minutes (PK-0305-NC, Takasago Electric, Inc.). The animals were artificially ventilated at a constant volume (3–4 ml). Tracheal pressure was recorded with a side-arm of the cannula connected to a pressure transducer (MFP-1, Nihon Kohden Kogyo Co., Ltd.). Test compounds or vehicles were administered i.v. (0.03 ml/100 g) 5 minutes or p.o. (0.5 ml/100 g) 1 hour prior to the intraveneous injection of LT04 (1 $\mu$g/kg). All compounds were injected through the cannulated jugular vein. The peak bronchoconstriction of each animal was determined as the percentage of the maximal pressure obtained by clamping off the trachea at the end of each experiment.

The inhibitory effect of the test compounds were expressed as follows: % of inhibition=(1-T/C)×100 wherein T and C are the average peak bronchoconstrictions for the compounds of the present invention and the vehicle, respectively.

The 50% effective doses (ED50, mg/kg) were calculated graphically.

The results are shown in Table 1.

TABLE 1

| Compounds | The inhibition of contractions of guinea pig terminal ileum induces with LTD4 [IC50 (g/ml)] | Action of Bronchoconstriction in guinea pigs induced with LTD4 [ED50 (mg/kg)] po | iv |
|---|---|---|---|
| A | $2.2 \times 10^{-9}$ | 1.3 | 0.037 |
| B | $1.1 \times 10^{-10}$ | 0.8 | 0.0054 |
| C | $2.5 \times 10^{-9}$ | 0.7 | 0.03 |
| D | $6.6 \times 10^{-11}$ | 1.0 | 0.0023 |
| E | $6.0 \times 10^{-10}$ | 1.9 | 0.006 |
| F | $4.0 \times 10^{-10}$ | 2.2 | 0.014 |
| G | $3.6 \times 10^{-10}$ | 1.6 | 0.0012 |
| H | $1.8 \times 10^{-10}$ | 2.0* | 0.01 |
| I | $7.6 \times 10^{-11}$ | 2.5* | 0.0023 |
| J | $9.0 \times 10^{-11}$ | 0.46 | 0.0046 |
| K | $3.1 \times 10^{-10}$ | 0.25 | 0.0036 |
| L | $2.5 \times 10^{-8}$ | 22.0 | 0.28 |

EXPERIMENT EXAMPLE 3: ACUTE TOXICITY

The compound of Example 1 of the present invention was intraveneously (iv) or orally (po) administered to a group of male ddy mice once. After 10 days, the $LD_{50}$ values were determined by the Litchfield-Wilcoxon method. The results are shown in Table 2.

TABLE 2

| Route | $LD_{50}$ (mg/kg) |
|---|---|
| iv | >300 |
| po | >1000 |

According to the foregoing pharmacological experimental examples and various pharmacological or toxicological experiments, the compounds of formula(I) of the present invention and their pharmaceutically acceptable salts and esters possess potent and long-lasting leukotriene-antagonistic actions and inhibitory actions against leukotrienes, and also exhibit better absorption by the oral administration.

Further, the compounds of the present invention possess 5-lipoxygenase-inhibitory actions and/or cyclooxygenase-inhibitory actions, inhibitory actions to biosynthesis of LTB4, chemotactic actions against human leucocyte, chymase-inhibitory actions, inhibitory actions to release of histamine or anti-histamine actions.

Therefore, they are useful as the prophylactic and therapeutic medicines for bronchial asthma, chronic bronchitis, atopic dermatitis, allergic rhinitis, allergic arthritis, allergic conjunctivitis, hay fever, urticaria, alimentary allergy, pain, pyretolysis, rheumatoid, thrombosis, coronary vascular diseases, ischemic heart disease, peptic or duodenal ulcer and the like.

The compounds of the present invention, their pharmaceutically acceptable salts and esters can be safely administered orally or parenterally to human beings in the form of a pharmaceutical composition such as tablets, pills, powder, capsules, granules, solutions, inhalants, suppositories, percutaneous absorption preparations or injectable solutions. The pharmaceutical compositions can be prepared by, for example, mixing a therapeutically effective amount of at least one compound of the present invention with a pharmaceutically acceptable additives such as an excipient, a carrier, a diluent or a solubilizer.

The dose may vary depending upon the compound selected or employed, the sex, age, weight and symptoms of patients to be treated, but the daily dose for human adults preferably ranges from 5 to 300 mg in single or multiple dose.

EXAMPLE 1

(1) To a suspension of 1.1 g of 60% sodium hydride in 30 ml of dimethyl sulfoxide under stirring at 70° C. for 30 minutes was added 4.1 g of 4-(4-methylphenyl)-butanol at room temperature and stirred for 30 minutes. To a mixture was added 40 ml of tetrahydrofuran and was cooled at 0° C. To the resulting mixture was added dropwise a solution of 3.9 g of 6-chloromethyl-2-formylpyridine in 40 ml of tetrahydrofuran. After completion of the addition, the mixture was stirred at the same temperature for 30 minutes and further was stirred at room temperature for 4 hours. After completion of the reaction, the reaction mixture was poured into water, extracted with ethyl acetate and washed with water. The organic layer was dried over anhydrous magnesium sulfate and the solvent was distilled off under reduced pressure to give a residue as an oily substance. The residue was purified by column chromatography on silica gel by passing chloroform and methanol(100:1) to give 1.3 g of 6-[4-(4-methylphenyl) butoxy]methyl-2-formylpyridine.

To a suspension of 1.94 g of Wittig reagent prepared by stirring 3-nitrobenzyl chloride and triphenylphosphine in 5 ml of tetrahydrofuran under ice-cooling was added dropwise a solution of 1.0M lithium bis(trimethylsilyl)amide in 5 ml of tetrahydrofuran. After completion of the addition, the mixture was heated up to room temperature, to the mixture was added 1.3 g of 6-[4-(4-methylphenyl)butoxy]methyl-2-formylpyridine as obtained above and further stirred for 5 hours. After completion of the reaction, an insoluble material was filtered off and the filtrate was concentrated under reduced pressure. The residue was purified by column chromatography on silica gel by passing chloroform and methanol (100:1) to give 0.36 g of 2-[(E)-2-(3-nitrophenyl)ethenyl]-6-[4-(4-methylphenyl) butoxy]ethylpyridine as an oily substance and 0.25 g of 2-[(Z)-2-(3-nitrophenyl)ethenyl]-6-[4-(4-methylphenyl)butoxy]methylpyridine as an oily substance, respectively.

(2) To 1.6 g of 2-[(E)-2-(3-nitrophenyl)ethenyl]-6-[4-(4-methylphenyl)butoxy]methylpyridine was added 10 ml of methanol and then added 3 g of stannous chloride dihydride in 10 ml of methanol, and the mixture was stirred under reflux for 3.5 hours. After completion of the reaction, the solvent was distilled off and the residue was made alkaline with an aqueous sodium hydroxide solution. To the solution was added ethyl acetate and the mixture was filtered by sellaite. The organic layer was separated, washed with water, and dried over anhydrous magnesium sulfate and then the solvent was distilled off to give 1.6 g of a crude oily substance. The crude oily substance was purified on chromatography by passing chloroform and then a mixture of chloroform and ethanol(50:1) to give 1.25 g of 2-[(E)-2-(3-aminophenyl)ethenyl]-6-[4-(4-methylphenyl) butoxy]methylpyridine as an oily substance.

On the other hand, by the use of 2-[(Z)-2-(3-nitrophenyl) ethenyl]-6-[4-(4-methylphenyl)butoxy]methylpyridine, the reaction was similarly carried out as the above-mentioned method to give 2-[(Z)-2-(3-aminophenyl)ethenyl]-6-[4-(4-methylphenyl)butoxy]methylpyridine.

(3) A solution of 1.25 g of 2-[(E)-2-(3-aminophenyl)ethenyl]-6-[4-(4-methylphenyl)butoxy]methylpyridine, 1.05 g of anhydrous diethyl succinate, 0.6 g of sodium acetate and 10 ml of dimethoxyethane was stirred under reflux for 5 hours. After completion of the reaction, the solvent was distilled off and to the residue was added water. After extracting with ethyl acetate, the organic layer was dried over anhydrous magnesium sulfate and the solvent was distilled off. To the residue was added isopropyl ether, the precipitated crystals were collected by filtration and recrystallized from ethanol to give 0.63 g of 2-[(E)-2-(3-(3-carboxy-3-ethylvalerylamino)-phenyl)ethenyl]-6-[4-(4-methylphenyl)butoxy]methylpyridine, melting at 141°–142° C. as white crystals.

EXAMPLE 2

By the use of 1.7 g of 2-[(Z)-2-(3-aminophenyl)ethenyl]-6-[4-(4-methylphenyl)butoxy]methylpyridine obtained in Example 1(2), 1.1 g of anhydrous diethyl succinate, 0.75 g of sodium acetate and 10 ml of dimethoxyethane, the reaction was similarly carried out as Example 1(3). The obtained crystals was recrystallized from 50% an aqueous ethanol to give 0.86 g of 2-[(Z)-2-(3-(3-carboxy-3-ethylvalerylamino)phenyl)ethenyl]-6-[4-(4-methylphenyl)butoxy]methylpyridine, melting at 114°–116° C. as white crystals.

EXAMPLE 3

By the use of 2.97 g of 2-[(E)-2-(3-aminophenyl)ethenyl]-6-[4-(4-butylphenyl)butylthio]methylpyridine, 1.6 g of anhydrous diethyl succinate, 0.85 g of sodium acetate and 10 ml of dimethoxyethane, the reaction was similarly carried out as Example 1(3). The obtained crystals were recrystallized from 50% an aqueous ethanol to give 2.4 g of 2-[(E)-2-(3-(3 carboxy-3-ethylvalerylamino)phenyl)ethenyl]-6-[4-(4-butylphenyl)butylthio]methylpyridine, melting at 150°–151° C. as white crystals.

EXAMPLE 4

To a solution of 1.0 g of 2-[(E)-2-(3-(3-carboxy-3-ethylvalerylamino)phenyl)ethenyl]-6-[4-(4-butylphenyl)butylthio]methylpyridine in 15 ml of dichloromethane was added 0.39 g of m-chloroperbenzoic acid at room temperature, and stirred for 7 hours. The reaction solution was washed with sodium carbonate, and the organic layer was dried over anhydrous magnesium sulfate and the solvent was distilled off. To the residue was added isopropyl ether and the precipitated crystals were collected by filtration. To a solution of the obtained crude crystals in methanol was added an activated charcoal. The activated charcoal was filtered off and the filtrate was distilled off. To the residue was added isopropyl ether and the mixture was filtered to give 0.84 g of 2-[(E)-2-(3-(3-carboxy-3-ethylvalerylamino)phenyl)ethenyl]-6-[4-(4-butylphenyl)butylsuylfonyl]methylpyridine, melting at 132°–134° C. as white crystals.

EXAMPLE 5

By the use of 0.54 g of 2-[(E)-2-(3-(3-carboxy-3-ethylvalerylamino)phenyl)ethenyl]-6-[(4-(4-butylphenyl)butylsulfinyl]methylpyridine, 0.21 g of m-chloroperbenzoic acid and 10 ml of dichloromethane, the reaction was similarly carried out as Example 4. To the obtained residue was added ethanol and the precipitated crystals were collected by filtration to give 0.16 g of 2-[(E)-2-(3-(3-carboxy-3-ethylvalerylamino)phenyl)ethenyl]-6-[4-(4-butylphenyl) butylsulfonyl]methylpyridine ½ hydrate, melting at 155°–157° C. with decomposition as white crystals.

EXAMPLE 6

By the use of 0.43 g of 2-[(E)-2-(3-aminophenyl)ethenyl]-6-[4-(4-methoxyphenyl)butoxy]methylpyridine, 0.24 g of anhydrous dimethyl glutamate, 0.31 g of sodium acetate and 10 ml of dimethoxyethane, the reaction was similarly carried out as Example 1(3). To the obtained residue were added isopropyl ether and n-hexane and then the residue was collected by filtration. Further, the residue was dissolved in chloroform, and filtered off and then the solvent was distilled off. To the residue were added isopropyl ether and n-hexane and the mixture was filtered off to give 0.3 g of 2-[(E)-2-(3-(4-carboxy-4-methylvalerylamino)phenyl)ethenyl]-6-[4-(4-methoxyphenyl)butoxy]methylpyridine, melting at 141°–142° C. as white crystals.

EXAMPLE 7

To a solution of 0.15 g of 2-[(E)-2-(3-(3-carboxy-3-ethylvalerylamino)phenyl)ethenyl]-6-[4-(4-methylphenyl) butoxy]methylpyridine in 6 ml of chloroform was added 0.15 g of thionyl chloride and the mixture was stirred under reduced pressure for 40 minutes. After completion of the reaction, the solvent was distilled off, to the residue was added a dilute sodium hydride and the mixture was extracted with ethyl acetate. The organic layer was washed with water, dried over anhydrous magnesium sulfate and the solvent was distilled off. To a solution of the residue in chloroform was added ethanolic hydrochloric acid and the solvent was distilled off to give 0.14 g of 2-[(E)-2-(3-(3-ethoxycarbonyl-3-ethylvalerylamino)phenyl) ethenyl]-6-[4-(4-methylphenyl)butoxy]methylpyridine hydrochloride ¼ hydrate as an amorphous solid.

|  | C | H | N |
|---|---|---|---|
| Theoretical value | 69.81 | 7.70 | 4.65 |
| Analytical value | 69.53 | 7.34 | 4.93 |

NMR(CDCl$_3$), δ ppm(base): 8.3(1H, s), 7.20–7.60(9H, m), 7.06(4H, s), 4.65(2H, s), 4.24(2H, q), 3.60(2H, m), 2.65(4H, m), 2.30(3H, s), 1.70(8H, m), 1.30(3H, t), 0.95(6H, q)

EXAMPLE 8

A mixture of 0.43 g of 2-[(E)-2-(3-aminophenyl)ethenyl]-6-[4-(4-bromophenyl)butoxy]methylpyridine, 0.24 g of anhydrous cyclohexyl succinate, 0.16 g of sodium acetate and 10 ml of dimethoxyethane was stirred under reduced pressure for 2 hours and then the reaction was similarly carried out as Example 1(3). The obtained crystals were recrystallized from 50% an aqueous ethanol to give 0.38 g of 2-[(E)-2-(3-(1-carboxy cyclohexylacetylamino)phenyl)ethenyl]-6-[4-(4-bromophenyl). butoxy]methylpyridine, melting at 164°–166° C. with decomposition as white crystals.

EXAMPLE 9

To a mixture of 0.35 g of 2-[(E)-2-(3-aminophenyl)ethenyl]-6-[4-(4-butylphenyl)butoxy]methylpyridine, 0.09 g of triethylamine and 5 ml of dichloromethane was added 0.15 g of ethyl succinyl chloride. After stirring at room temperature for 30 minutes, the reaction mixture was washed with water. The organic layer was dried over anhydrous magnesium sulfate and the solvent was distilled off to give 0.4 g of an oily substance. The oily substance was purified by column chromatography by passing chloroform and then a mixture of chloroform and ethanol(50:1). To a solution of the obtained oily substance in chloroform was added ethanolic hydrchloric acid and the solvent was distilled off. To the residue was added isopropyl ether and the pricipitated crystals were collected by filtration and further recrystallized from the mixed solvent of ethanol and isopropyl ether to give 0.3 g of 2-[(E)-2-(3-(3-ethoxycarbonylpropionylamino)phenyl)ethenyl]-6-[4-(4-butylphenyl)butoxy]methylpyridine hydrochloride 5/2 hydrate, melting at 100°-105° C. as light yellow crystals.

The following compounds can be prepared in a similar manner mentioned in Examples 1 to 9.

2-[(Z)-2-(3-(3-carboxy-3-ethylvalerylamino)phenyl)ethenyl]-6-(4-methylphenoxy)methylpyridine, melting at 134°-135° C.

2-[(E)-2-(3-(3-carboxy-3-ethylvalerylamino)phenyl)ethenyl]-6-(4-methylphenylthio)methylpyridine, melting at 146°-148° C.

2-[(E)-2-(3-(3-carboxy-3-ethylvalerylamino)phenyl)ethenyl]-6-[(4-(4-methoxyphenyl)butoxy]methylpyridine, melting at 118°-112° C. with decomposition 2-[(E)-2-(3-(3-carboxy-3-ethylvalerylamino)phenyl)ethenyl]-6-(4-hydroxy-3,5-di-tert-butylphenylthio)methylpyridine, melting at 203°-204° C.

2-[(E)-2-(3-(4-carboxy-4-methylvalerylamino)phenyl)ethenyl]-6-(4-methylphenylthio)methylpyridine hydrochloride hydrate, melting at 144°-146° C. with decomposition 2-[(E)-2-(3-(3-carboxy-3-ethylvalerylamino)phenyl)ethenyl]-6-(4-tert-butylphenoxy)methylpyridine, melting at 180°-182° C.

2-[(E)-2-(3-(3-carboxy-3-ethylvalerylamino)phenyl)ethenyl]-6-(2-methylphenylthio)methylpyridine, melting at 154°-155° C.

2-[(E)-2-[3-(3-carboxy-3-ethylvalerylamino)phenyl)ethenyl]-6-[4-(4-hydroxyphenyl)butoxy]methylpyridine ½ hydrate, melting at 110°-113° C.

2-[(E)-2-(3-(3-carboxy-3-ethylvalerylamino)phenyl)ethenyl]-6-(3-methylphenylthio)methylpyridine, melting at 160°-161° C.

2-[(E)-2-(3-(3-carboxy-3-ethylvalerylamino)phenyl)ethenyl]-6-(3,4,5-trimethoxyphenoxy)methylpyridine, melting at 181°-183° C.

2-[(E)-2-(3-(3-carboxy-3-ethylvalerylamino)phenyl)ethenyl]-6-(3-phenylpropylthio)methylpyridine ½ hydrate, melting at 133°-134° C. with decomposition 2-[(E)-2-(3-(3-carboxy-3-ethylvalerylamino)phenyl)ethenyl]-6-(4-cyclohexylbutoxy)methylpyridine, melting at 171°-173° C., with decomposition 2-[(E)-2-(3-(4-carboxy-4-methylvalerylamino)phenyl)ethenyl]-6-(4-cyclohexylbutoxy)methylpyridine, melting at 168°-170° C. with decomposition 2-[(E)-2-(3-(3-carboxy-3-ethylvalerylamino)phenyl)ethenyl]-6-[4-(4-isopropylphenyl)butoxy]methylpyridine, melting at 138°-140° C. with decomposition 2-[(E)-2-(3-(3-carboxy-3-ethylvalerylamino)phenyl)ethenyl]-6-(4-phenylbutoxy)methylpyridine ½ hydrate, melting at 126°-127° C. with decomposition 2-[(E)-2-(3-(4-carboxy-4-methylvalerylamino)phenyl)ethenyl]-6-[4-(4-butylphenyl)butoxy]methylpyridine, melting at 147°-149° C. with decomposition 2-[(E)-2-(3-(3-carboxy-3-ethylvalerylamino)phenyl)ethenyl]-6-[4-(4-butylphenyl)butoxy]methylpyridine, melting at 124°-126° C. with decomposition 2-[(E)-2-(3-(3-carboxy-3-ethylvalerylamino)phenyl)ethenyl]-6-(3,4-dimethylphenoxy)methylpyridine ¼ hydrate, melting at 175°-177° C. with decomposition 2-[(E)-2-(3-(3-carboxy-3-ethylvalerylamino)phenyl)ethenyl]-6-[4-(4-fluorophenyl)butoxy]methylpyridine ½ hydrate, melting at 139°-141° C. with decomposition 2-[(E)-2-(3-(4-carboxy-4-methylvalerylamino)phenyl)ethenyl]-6-(4-tertbutylphenoxy)methylpyridine ¼ hydrate, melting at 160°-163° C. with decomposition 2-[(E)-2-(3-(3-carboxy-3-ethylvalerylamino)phenyl)ethenyl]-6-(4-methylphenoxy)methylpyridine, melting at 161°-163° C. with decomposition 2-[(E)-2-(3-(4-carboxy-4-methylvalerylamino)phenyl)ethenyl]-6-(4-methylphenoxy)methylpyridine, melting at 177°-179° C. with decomposition 2-[(E)-2-(3-(3-carboxy-3-ethylvalerylamino)phenyl)ethenyl]-6-[4-(4-isobutylphenyl)butoxy]methylpyridine, melting at 156°-157° C. with decomposition 2-[(E)-2-(3-(3-carboxy-3-ethylvalerylamino)phenyl)ethenyl]-6-[4-(4-ethylphenyl)butoxy]methylpyridine, melting at 145°-147° C. with decomposition 2-[(E)-2-(3-(3-carboxy-3-ethylvalerylamino)phenyl)ethenyl]-6-[4-(4-bromophenyl)butoxy]methylpyridine, melting at 140°-141° C. with decomposition 2-[(E)-2-(3-(3-carboxy-3-ethylvalerylamino)phenyl)ethenyl]-6-(3-phenylpropoxy)methylpyridine ¼ hydrate, melting at 181°-182° C. with decomposition 2-[(E)-2-(3-ethoxalylaminophenyl)ethenyl]-6-(4-hydroxy-3,5-di-tertbutylphenylthio)methylpyridine hydrochloride ¼ hydrate, melting at 140°-143° C. with decomposition 2-[(E)-2-(3-(1-carboxycyclohexyl)acetylaminophenyl)ethenyl]-6-(4-phenylbutoxy)methylpyridine 2 hydrate, melting at 117°-120° C. with decomposition 2-[(E)-2-(3-(3-carboxy-3-ethylvalerylamino)phenyl)ethenyl]-6-[4-(3,4-dimethoxyphenyl)butoxy]methylpyridine, melting at 119°-122° C. with decomposition 2-[(E)-2-(3-(3-carboxy-3-ethylvalerylamino)phenyl)ethenyl]-6-[4-(3,4-dihydroxyphenyl)butoxy]methylpyridine 2-[(E)-2-(3-(3-carboxy-3-ethylvalerylamino)phenyl)ethenyl]-6-[4-(4-ethoxyphenyl)butoxy]methylpyridine, melting at 116°-118° C. with decomposition 2-[(E)-2-(3-(3-carboxy-3-ethylvalerylamino)phenyl)ethenyl-6-[4-(4-butoxyphenyl)butoxy]methylpyridine 3/2 hydrate, melting at 120°-124° C. with decomposition 2-[(E)-2-(3-(3-carboxy-3-ethylvalerylamino)phenyl)ethenyl]-6-[4-(4-propoxyphenyl)butoxy]methylpyridine, melting at 123°-124° C. with decomposition 2-[(E)-Z-(3-(3-carboxy-3-ethylvalerylamino)phenyl)ethenyl]-6-[4-(4-hexylphenyl)butoxy]methylpyridine, melting at 127°-129° C. with decomposition 2-[(E)-2-(3-(1-carboxycyclohexyl)acetylaminophenyl)ethenyl]-6-[4-(4-butylphenyl)butoxy]methylpyridine, melting at 167°-169° C.

2-[(E)-2-(3-(3-carboxy-3-ethylvalerylamino)phenyl)ethenyl-6-[4-(3,5-dimethyl-4-methoxyphenyl)butoxy]methylpyridine 2-(E)-2-(3-(3-carboxy-3-ethylvalerylamino)phenyl)ethenyl]-6-[4-(4-hydroxy-3,5-dimethylphenyl)butoxy]methylpyridine 2-[(E)-2-(3-(3-carboxy-3-ethylvalerylamino)phenyl)ethenyl]-6-[4-((4-chlorophenyl)phenylmethyl)-1-piperazinyl]methylpyridine ¼ hydrate, melting at 165°-167° C. with decomposition 2-[(E)-2-(3-(3-carboxy-3-ethylvalerylamino)phenyl)ethenyl]-6-(4-diphenylmethyl-1-piperazinyl)methylpyridine, melting at 171°-173° C. with decomposition 2-[(E)-2-(3-(3-carboxy-3-ethylvalerylamino)phenyl)ethenyl]-6-[4-bis(4-fluorophenyl)methyl-1-piperazinyl]methylpyridine, melting at 163°-164° C. with decomposition 2-[(E)-2-(3-(3-carboxy-3-ethylvalerylamino)phenyl)ethenyl]-6-[4-(4-fluorobenzyl)-1-piperazinyl]methylpyridine ¼ hydrate, melting at 135°-138° C. with decomposition 2-[(E)-2-(3-(3-carboxy-3-ethylvalerylamino)phenyl)ethenyl]-6-[4-(4-methylphenylsulfonyl)-1-piperazinyl]methylpyridine, melting at 139°-142° C. with decomposition 2-[(E)-2-(3-(3-carboxy-3-ethylvalerylamino)phenyl)ethenyl]-6-[2-(4-chlorophenylsulfonylamino)ethoxy]methylpyridine ¼ hydrate, melting at 82°-85° C. with decomposition 2-[(E)-2-(3-(3-carboxy-3-ethylvalerylamino)phenyl)ethenyl]-6-[4-(4-methylphenylsulfonylamino)piperidino]methylpyridine, melting at 115°-118° C. with decomposition 2-[(E)-2-(3-(3-carboxy-3-ethylvalerylamino)phenyl)ethenyl]-6-[4-(3-pyridylmethyl)-1-piperazinyl]methylpyridine hydrate, melting at 87°-89° C. with decomposition 2-[(E)-2-(3-(3-carboxy-3-ethylvalerylamino)phenyl)ethenyl]-6-[1-(phenylethyl)-4-piperidinylcarbamoyl]methylpyridine 2-[(E)-2-(3-(3-carboxy-3-ethylvalerylamino)phenyl)ethenyl]-6-(1-pyrrolidinyl)methylpyridine hydrate, melting at 161°-163° C. with decomposition 2-[2-(3-(3-carboxy-3-ethylvalerylamino)phenyl)ethenyl]-6-(4-phenyl-1-butenyl)pyridine, melting at 148°-149° C.

2-[(E)-2-(3-(3-carboxy-3-ethylvalerylamino)phenyl)ethenyl]-6-[(1,4-benzodioxan-2-yl)methoxy]methylpyridine, melting at 167°-169° C. with decomposition 2-(3-carboxy-3-ethylvalerylamino)-4'-[4-(4-ethylphenyl) butoxy]-(E)-stilbene, melting at 114°-115° C.

3-(3-carboxy-3-ethylvalerylamino)-3'-[4-(4-ethylphenyl) butoxy]-(E)-stilbene, melting at 119°-121° C.

3-(1-carboxycyclopentylacetylamino)-3'-[4-(4-ethylphenyl) butoxy]-(E)-stilbene ¼ hydrate, melting at 96°-99° C.

3-(1-carboxycyclohexylacetylamino)-3'-[4-(4-ethylphenyl) butoxy]-(E)-stilbene, melting at 102°-105° C.

3-(3-carboxy-3-ethylvalerylamino)-3'-[4-(4-n-butylphenyl) butoxy]-(E)-stilbene, melting at 122°-125° C.

2-[(E)-2-(3-(3-carboxy-3-ethylvalerylamino)phenyl)ethenyl]-6-[4-(4-propylphenyl)butoxy]methylpyridine ¼ hydrate, melting at 130°-134° C. with decomposition 2-[(E)-2-(3-(1-carboxycyclohexylacetylamino)phenyl)ethenyl]-6-[4-(4-ethoxyphenyl)butoxy]methylpyridine, ¼ hydrate, melting at 122°-124° C. with decomposition 2-[(E)-2-(3-(1-carboxycyclopentylacetylamino)phenyl)ethenyl]-6-[4-(4-ethoxyphenyl)butoxy]methylpyridine ¼ hydrate, melting at 118°-121° C. with decomposition 2-[(E)-2-(3-(3-carboxy-3-ethylvalerylamino)phenyl)ethenyl]-6-[4-(4-allyloxyphenyl)butoxy]methylpyridine 3/2 hydrate, melting at 108°-112° C. with decomposition 2-[(E)-2-(3-(3-carboxy-3-ethylvalerylamino)phenyl)ethenyl]-6-[4-(4-tert-butylphenyl)butoxy]methylpyridine, melting at 160°-162° C.

2-[(E)-2-(3-(3-carboxy-3-ethylvalerylamino)phenyl)ethenyl]-6-[4-(4-chlorophenyl)butoxy]methylpyridine, melting at 132°-133° C. with decomposition 2-[(E)-2-(3-(1-carboxycyclopentylacetylamino)phenyl)ethenyl]-6-[4-(4-butoxyphenyl)butoxy]methylpyridine ¼ hydrate, melting at 132°-134° C. with decomposition 2-[(E)-2-(3-(1-carboxycyclohexylacetylamino)phenyl)ethenyl]-6-[4-(4-tert-butylphenyl)butoxyl]methylpyridine ¼ hydrate, melting at 130°-132° C. with decomposition 2-[(E)-2-(3-(1-carboxycyclopentylacetylamino)phenyl)ethenyl]-6-[4-(4-tert-butylphenyl)butoxyl]methylpyridine ¼ hydrate, melting at 129°-131° C. with decomposition 2-[(E)-2-(3-(3-carboxy-3-ethylvalerylamino)phenyl)ethenyl]-6-[4-(4-cyclopropylmethoxyphenyl)butoxy]methylpyridine, melting at 120°-122° C. with decomposition 2-[(E)-2-(3-(3-carboxy-3-ethylvalerylamino)phenyl)ethenyl]-6-[4-(4-pentyloxyphenyl)butoxy]methylpyridine ⅜ hydrate, melting at 112°-115° C. with decomposition 2-[(E)-2-(3-(3-carboxy-3-ethylvalerylamino)phenyl)ethenyl]-6-[4-(4-cyclopentyloxyphenyl)butoxy]methylpyridine ¼ hydrate, melting at 140°-141° C. with decomposition 2-[(E)-2-(3-(3-carboxy-3-ethylvalerylamino)phenyl)ethenyl]-6-[4-(4-isobutoxyphenyl)butoxy]methylpyridine ¼ hydrate, melting at 130°-131° C. with decomposition 3-(3-carboxy-3-ethylvalerylamino)-3'-[4-(4-ethenylphenyl) butoxymethyl]-(E)-stillbene, melting at 105°-107° C.

3-(3-carboxy-3-ethylvalerylamino)-3'-[4-(4-n-butylphenyl) butoxymethyl]-(E)-stillbene, melting at 109°-111° C.

2-[(E)-2-[3-(3-carboxy-3-ethylvalerylaminophenyl]ethenyl]-6-[4-(4-isopentyloxyphenyl)butoxy]methylpyridine ¼ hydrate, melting at 120°-122° C. with decomposition 2-[(E)-2-[3-(3-carboxy-3-ethylvalerylamino)phenyl]ethenyl]-6-(6-phenylhexyl)pyridine, melting at 160°-161° C. with decomposition 2-[(E)-2-[3-(3-carboxy-3-ethylvalerylamino)phenyl]ethenyl]-6-[6-(4-ethylphenyl)hexyl]pyridine 2-[(E)-2-[3-(3-carboxy-3-ethylvalerylamino)phenyl]ethenyl]-6-[6-(4-n-butylphenyl)hexyl]pyridine 2-[(E)-2-[3-(3-carboxy-3-ethylvalerylamino)phenyl]ethenyl]-6-[6-(4-n-butoxyphenyl)hexyl]pyridine 2-[(E)-2-[3-(3-carboxy-3-ethylvalerylamino)phenyl]ethenyl]-6-[6-(4-isopentyloxyphenyl)hexyl]pyridine 2-[(E)-2-[3-(3-carboxy-3-ethylvalerylamino)phenyl]ethenyl]-6-(5-phenylpentyloxy)pyridine, melting at 136°-137° C.

2-[(E)-2-[3-(3-carboxy-3-ethylvalerylamino)phenyl]ethenyl]-6-[5-(4-ethylphenyl)pentyloxy]pyridine 2-[(E)-2-[3-(3-carboxy-3-ethylvalerylamino)phenyl]ethenyl]-6-[5-(4-n-butylphenyl)pentyloxy]pyridine 2-[(E)-2-[3-(3-carboxy-3-ethylvalerylamino)phenyl]ethenyl]-6-[5-(4-n-butoxyphenyl)pentyloxy]pyridine 2-[(E)-2-[3-(3-carboxy-3-ethylvalerylamino)phenyl]ethenyl]-6-[5-(4-isopentyloxyphenyl)pentyloxy]pyridine 2-[(E)-2-[3-(3-carboxy-3-ethylvalerylamino)phenyl]ethenyl]-6-[4-(4-ethylphenyl)butoxy]pyridine 2-[(E)-2-[3-(3-carboxy-3-ethylvalerylamino)phenyl]ethenyl]-6-[4-(4-n-butylphenyl)butoxy]pyridine 2-[(E)-2-[3-(3-carboxy-3-ethylvalerylamino)phenyl]ethenyl]-6-[4-(4-n-butoxyphenyl)butoxy]pyridine 2-[(E)-2-[3-(3-carboxy-3-ethylvalerylamino)phenyl]ethenyl]-6-[4-(4-isopentyloxyphenyl)butoxyl]pyridine 2-[(E)-2-[3-(3-carboxy-3-ethylvaleryamino)phenyl]ethenyl]-6-[4-(3-n-butoxylphenyl)butoxy]pyridine 2-[(E)-2-[3-(3-carboxy-3-ethylvalerylamino)phenyl]ethenyl]-6-[4-(2-n-butoxyphenyl)butoxy]pyridine 2-[(E)-2-[3-(3-carboxy-3-ethylvalerylamino)phenyl]ethenyl]-6-[4-(4-(2-phenylethoxy)phenyl)butoxy]pyridine 2-[(E)-2-[3-(3-carboxy-3-ethylvalerylamino)phenyl]ethenyl]-6-[4-(4 (3-pyridylmethoxy)phenyl]butoxyl]methylpyridine 2-[(E)-2-[3-(3-carboxy-3-ethylvalerylamino)phenyl]ethenyl]-6-[4-(4-(3-(1-imidazolyl)propoxy)phenyl)butoxy]methylpyridine 2-[(E)-2-3-(3-carboxy-3-ethylvalerylamino)phenyl]ethenyl]-7-[4-(4-ethylphenyl)butyl]quinoline 2-[(E)-2-[3-(3-carboxy-3-ethylvalerylamino)phenyl]ethenyl]-7-[3-(4-ethylphenyl)propoxy]quinoline 2-[(E)-2-[3-(3-carboxy-3-ethylvalerylamino)phenyl]ethenyl]-7-[4-(4-ethylphenyl)butoxy]quinoline 2-[(E)-2-[3-(3-carboxy-3-ethylvalerylamino)phenyl]ethenyl]-7-(4-phenylbutoxy)methylquinoline 2-[(E)-2-[3-(3-carboxy-3-ethylvalerylamino)phenyl]ethenyl]-6-[4-(4-cyclopropylphenyl)butoxy]methylpyridine 2-[(E)-2-[3-(3-carboxy-3-ethylvalerylamino)phenyl]ethenyl]-6-[4-(4-cyclobutylphenyl)butoxy]methylpyridine 2-[(E)-2-[3-(3-carboxy-3-ethylvalerylamino)phenyl]ethenyl]-6-[4-(4-isopropoxylphenyl)butoxy]methylpyridine 2-[(E)-2-[3-(3-carboxy-3-ethylvalerylamino)phenyl]ethenyl]-6-[4-(4-tert-butoxyphenyl)butoxy]methylpyridine 2-[(E)-2-[3-(3-carboxy-3-ethylvalerylamino)-phenylethenyl-6-[4-(4-cyclopropoxyphenyl)butoxy]methylpyridine 2-[(E)-2-[3-(3-carboxy-3-ethylvalerylamino)phenyl]ethenyl]-6-[4-(4-cyclobutoxyphenyl)butoxy]methylpyridine 2-[(E)-2-[3-(3-carboxy-3-ethylvalerylamino)phenyl]ethenyl]-6-[4-(4-cyclobutylmethoxyphenyl)butoxy]methylpyridine 2-[(E)-2-[3-(3-carboxy-3-ethylvalerylamino)phenyl]ethenyl]-6-[4-(4-(2-propynyloxy)phenyl)butoxyl]methylpyridine 2-[(E)-2-[3-(3-carboxy-3-ethylvalerylamino)phenyl]ethenyl]-6-[4-(3,4-dihydroxyphenyl)butoxy]methylpyridine 2-[(E)-2-[3-(3-carboxy-3-ethylvalerylamino)phenyl]ethenyl]-6-[4-(4-hydroxy-3-methylphenyl)butoxy]methylpyridine 2-[(E)-2-[3-(3-carboxy-3-ethylvalerylamino)phenyl]ethenyl]-6-[4-(4-hydroxy-3,5-dimethylphenyl)butoxy]methylpyridine 2-[(E)-2-[3-(3-carboxy-3-ethylvalerylamino)phenyl]ethenyl]-6-[4-(4-hydroxy-3,5-di-tert-butylphenyl)butoxy]methylpyridine 2-[(E)-2-[3-(3-carboxy-3-ethylvalerylamino)phenyl]ethenyl]-6-[6-(4-hydroxy-3,5-di-tert-butylphenyl)hexyl]pyridine 2-[(E)-2-[3 (3-carboxy-3-ethylvalerlyamino)phenyl]ethenyl]-6-[6-(3,4-dihydroxyphenyl)hexyl]pyridine 2-[(E)-2-[3-(3-carboxy-3-ethylvalerylamino)phenyl]ethenyl]-6-[6-(4-hydroxy-3-methylphenyl)hexyl]pyridine 2-[(E)-2-[3-(3-carboxy-3-ethylvalerylamino)phenyl]ethenyl]-6-[6-(4-hydroxy-3,5-dimethylphenyl)hexyl]pyridine 2-[(E)-2-[3-(3-carboxy-3-ethylvalerylamino)phenyl]ethenyl]-6-[5-(4-hydroxy-3,5-dimethylphenyl)pentyloxy]pyridine 2-[(E)-2-[3-(3-carboxy-3-ethylvalerylamino)phenyl]ethenyl]-6-[4-(4-hydroxy-3,5-dimethylphenyl)butoxy]pyridine 2-[(E)-2-[3-(3-carboxy-3-ethylvalerylamino)phenyl]ethenyl]-6-[4-(4-hydroxy-3-methylphenyl)pentyloxy]pyridine 2-[(E)-2-[3-(3-carboxy-3-ethylvalerylamino)phenyl]ethenyl]-6-[3-(4-hydroxy-3,5-di-tert butylphenoxy)propoxy]methylpyridine

EXAMPLE 10: PHARMACEUTICAL PREPARATION(CAPSULES)

| | |
|---|---|
| Compound Example 1 | 20 g |
| Crystalline cellulose | 65 g |
| Corn starch | 20 g |
| Lactose | 22 g |
| Polyvinylpyrrolidone | 3 g |
| Total | 130 g |

The above-mentioned components were granulated by the conventional method and then the obtained granules were filled into 1000 capsules of gelatin soft capsule.

Each of these capsules contain of 20 mg of the compound of Example 1 as an active ingredient.

EXAMPLE 11: PHARMACEUTICAL PREPARATION(POWDERS)

| | |
|---|---|
| Compound of Example 1 | 50 g |
| Crystalline cellulose | 400 g |
| Corn starch | 550 g |
| Total | 1000 g |

The compound of Example 1 was dissolved in acetone, the solution was adsorbed by crystalline cellulose and then dried. The dried crystalline cellulose and corn starch were mixed and the powders containing of 20-fold powder of the compound of Example 1 were prepared by the conventional method.

EXAMPLE 12: PHARMACEUTICAL PREPARATION(TABLETS)

| | |
|---|---|
| Compound of Example 1 | 10 g |
| Corn strach | 10 g |
| Lactose | 20 g |
| Calcium carboxymethyl cellulose | 10 g |
| Crystalline cellulose | 35 g |
| Polyvinyl pyrrolidone | 5 g |
| Talc | 10 g |
| Total | 100 g |

The compound of Example 1 was dissolved in acetone, the solution was adsorbed by crystalline cellulose and then dried. The dried crystalline cellulose, corn starch, lactose and calcium carboxymethyl cellulose were mixed, an aqueous solution of polyvinyl pyrrolidone as a binder was added thereto and then the mixture was granulated by the conventional method. The thus obtained granules were mixed with talc as a lubricant and then tablets comprising 100 mg per tablet were prepared by means of a rotary pelletizing machine of the punching type. Each of tablets contain 10 mg of the compound of Example 1.

EXAMPLE 13: PHARMACEUTICAL PREPARATION(INJECTION)

| | |
|---|---|
| Compound of Example 1 | 10 g |
| Solubilizer Nikkol HCO-60 ® (produced by Nikko Chemical ltd.) | 37 g |
| Sesame oil | 2 g |
| Sodium chloride | 9 g |
| Propylene glycol | 40 g |
| Phosphate buffer (0.1 M, pH 6.0) | 100 g |
| distilled water | 802 g |
| Total | 1000 g |

The compound of Example 1, Nikkol HCO-60, Sesame oil and 20 g of propylene glycol were mixed and dissolved under heating at about 80° C. To the mixture were added a solution of sodium chloride and 20 g of propylene glycol dissolved in distilled water under heating at about 80° C. to give a total volume of 1000 ml of the aqueous solution. The aqueous solution was separated into 2 ml of amples, the amples were sealed by dissolution and sterilized under heating. Each of amples contain 20 mg of the compound of Example 1.

What is claimed is:

1. A styryl compound of the formula (I):

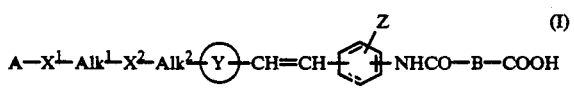

wherein A is phenyl substituted by at least one substituent selected from the group consisting of halogen, nitro, amino, monoalkylamino, dialkylamino, hydroxy, alkyl, cycloalkyl, alkenyl, alkenyloxy, alkynyl, aralkyl, alkoxy, halo-alkyl, cyano, alkanoylamino, alkylthio, alkylsulfonyl, alkylsulfonyl, acyl, carbamoyl, monoalkylcarbamoyl, dialkylcarbamoyl, carboxyalkanoylamino, alkoxycarbonylalkanoylamino, phenylsulfonyl, phenylsulfonylamino and a diphenylmethyl group of the formula (b), (c) or (d):

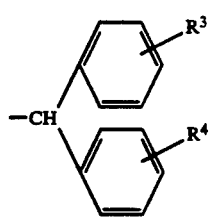

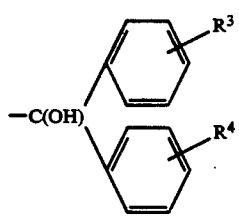

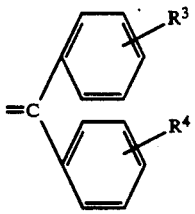

(wherein $R^3$ and $R^4$ are the same or different, and respectively represent hydrogen, halogen, halo-alkyl, amino, nitro, cyano, hydroxy, alkyl or aralkyl);

Alk1 is alkylene having 4 carbon atoms, and Alk 2 is alkylene having 1 carbon atom;

X1 is single bond and X2 is oxygen;

Y ring represents pyridyl;

B represents branched-chain alkylene having 6 carbon atoms;

Z represents hydrogen, halogen, alkyl, alkoxy, haloalkyl, alkylthio, alkylsulfinyl or alkylsulfonyl; a pharmaceutically acceptable salt or an ester thereof.

2. A styryl compound of the formula (I'):

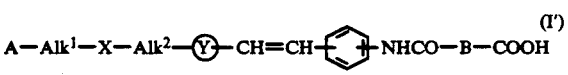

wherein A is phenyl substituted by at least one substituent selected from the group consisting of halogen, nitro, amino, hydroxy, alkyl, cycloalkyl, alkenyl, alkenyloxy, alkynyl, aralkyl, alkoxy, halo-alkyl, cyano, alkanoylamino, alkylthio, acyl, carbamoyl, carboxyalkanoylamino, phenylsulfonyl, phenylsulfonylamino and a diphenylmethyl group of the formula (b):

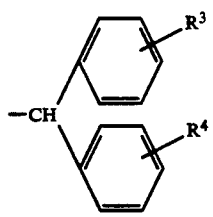

(wherein $R^3$ and $R^4$ are the same or different, and respectively represent hydrogen, halogen, halo-alkyl, amino, nitro, cyano, hydroxy, alkyl or aralkyl);

Alk1 is alkylene having 4 carbon atoms, and Alk2 is alkylene having 1 carbon atom;

X represents oxygen;

Y ring represents pyridyl;

B represents branched-chain alkylene having 6 carbon atoms;

a pharmaceutically acceptable salt or an ester thereof.

3. A compound selected from:
 (a) 2-[(E)-2-(3-(3-carboxy-4-ethylvalerylamino)-phenyl)ethenyl]-6-[4-(4-isopropylphenyl)butoxy]-methylpyridine
 (b) 2-[(E)-2-(3-(3-carboxy-3-ethylvalerylamino)-phenyl)ethenyl]-6-(4-phenylbutoxy)methylpyridine
 (c) 2-[(E)-2-(3-(3-carboxy-3-ethylvalerylamino)-phenyl)ethenyl]-6-[4-(4-butylphenyl)butoxy]methylpyridine (d) 2-[(E)-2-(3-(3-carboxy-3-ethylvalerylamino)-phenyl)ethenyl]-6-[4-(4-fluorophenyl)butoxy]methylpyridine
(e) 2-[(E)-2-(3-(3-carboxy-3-ethylvalerylamino)-phenyl)ethenyl]-6-[4-(4-isobutylphenyl)butoxy]methylpyridine
(f) 2-[(E)-2-(3-(3-carboxy-3-ethylvalerylamino)-phenyl)ethenyl]-6-[4-(4-ethylphenyl)butoxy]methylpyridine
(g) 2-[(E)-2-(3-(3-carboxy-3-ethylvalerylamino)-phenyl)ethenyl]-6-[4-(4-ethoxyphenyl)butoxy]methylpyridine
(h) 2-[(E)-2-(3-(3-carboxy-3-ethylvalerylamino)-phenyl)ethenyl]-6-[4-(4-butoxyphenyl)butoxy]methylpyridine
(i) 2-[(E)-2-(3-(3-carboxy-3-ethylvalerylamino)-phenyl)ethenyl]-6-[4-(4-propoxyphenyl)butoxy]methylpyridine
(j) 2-[(E)-2-(3-(3-carboxy-3-ethylvalerylamino)-phenyl)ethenyl]-6-[4-(4-propylphenyl)butoxy]methylpyridine or
(k) 2-[(E)-2-(3-(3-carboxy-3-ethylvalerylamino)-phenyl)ethenyl]-6-[4-(4-isopentyloxyphenyl)butoxy]methylpyridine 4. A compound selected from
(a) 2-[(E)-2-(3-(3-carboxy-3-ethylvalerylamino)-phenyl)ethenyl]-6-[4-(3,4-dihydroxyphenyl)butoxy]methylpyridine
(b) 2-[(E)-2-(3-(3-carboxy-3-ethylvalerylamino)-phenyl)ethenyl]-6-[4-(4-hydroxy-3-methylphenyl)butoxy]methylpyridine
(c) 2-[(E)-2-(3-(3-carboxy-3-ethylvalerylamino)-phenyl)ethenyl]-6-[4-(4-hydroxy-3,5-dimethylphenyl)butoxy]methylpyridine
(d) 2-[(E)-2-(3-(3-carboxy-3-ethylvalerylamino)-phenyl)ethenyl]-6-[4-(4-hydroxy-3,5-di-tert-butylphenyl)butoxy]methylpyridine or
(e) 2-[(E)-2-(3-(3-carboxy-3-ethylvalerylamino)-phenyl)ethenyl]-6-[4-(4-hydroxy-3,5-dimethylphenyl)butoxy]pyridine 5. A pharmaceutical composition comprising an effective amount of the compound of any one of claims 1, 2, 3 or 4 of a pharmaceutically acceptable salt or an ester thereof, and an inert carrier.

* * * * *